US011458414B2

(12) United States Patent
Lee (10) Patent No.: US 11,458,414 B2
(45) Date of Patent: Oct. 4, 2022

(54) METHODS AND APPARATUS UTILIZING VACUUM FOR BREAKING ORGANIC CELL WALLS

(71) Applicant: Synergy Burcell Technologies, LLC, Cordele, GA, Cordele, GA (US)

(72) Inventor: Olaf Lee, Forest Lake, MN (US)

(73) Assignee: Synergy Burcell Technologies, LLC, Cordele, GA (US)

( * ) Notice: Subject to any disclaimer, the term of this patent is extended or adjusted under 35 U.S.C. 154(b) by 1900 days.

(21) Appl. No.: 15/028,719

(22) PCT Filed: Oct. 12, 2014

(86) PCT No.: PCT/US2014/060208
§ 371 (c)(1),
(2) Date: Apr. 12, 2016

(87) PCT Pub. No.: WO2015/054682
PCT Pub. Date: Apr. 16, 2015

(65) Prior Publication Data
US 2016/0257923 A1    Sep. 8, 2016

Related U.S. Application Data

(60) Provisional application No. 61/971,949, filed on Mar. 28, 2014, provisional application No. 61/890,282, filed on Oct. 13, 2013.

(51) Int. Cl.
*B01D 5/00* (2006.01)
*C12M 1/33* (2006.01)
(Continued)

(52) U.S. Cl.
CPC ............... *B01D 5/006* (2013.01); *A01C 3/00* (2013.01); *B09B 3/00* (2013.01); *B09B 5/00* (2013.01); *C12M 45/02* (2013.01); *Y02A 20/00* (2018.01)

(58) Field of Classification Search
CPC .. B01D 5/006; B09B 5/00; B09B 3/00; A01C 3/00; C12M 45/02; Y02A 20/109
See application file for complete search history.

(56) References Cited

U.S. PATENT DOCUMENTS

| 1,536,894 A | 5/1925 | Lillie |
| 1,986,760 A | 1/1935 | Kreissler |

(Continued)

FOREIGN PATENT DOCUMENTS

| DE | 3150314 A1 | 7/1983 |
| DE | 19932403 A1 | 1/2001 |

(Continued)

*Primary Examiner* — Gregory D Swiatocha
(74) *Attorney, Agent, or Firm* — Alan D. Kamrath; Mayer & Williams PC (57) ABSTRACT

Moisturized organic material is treated by communicating with a vacuum pump (44) to selectively reduce pressure within a vessel (12) below atmospheric pressure and to a vaporization point, such as at 30 to 17.8° C., for a period of time sufficient to create an internal pressure to rupture cell walls. While being subjected to vacuum below atmospheric pressure, the vessel (12) is rotated to homogenize the moisturized organic material. The organic material can be moisturized by non-potable water including moisture collected by a moisture collector (44b) in the conduit (44a) between the vessel (12) and the vacuum pump (44) and by chilled feed water acting as the seal fluid in the vacuum pump and heated while flowing through a heat exchanger (148) of the moisture collector (44b). Heat can be added by a heater (46) to raise the temperature of low ambient temperature moisturized organic material.

18 Claims, 4 Drawing Sheets

(51) Int. Cl.
*A01C 3/00* (2006.01)
*B09B 3/00* (2022.01)
*B09B 5/00* (2006.01)

(56) References Cited

U.S. PATENT DOCUMENTS

| | | |
|---|---|---|
| RE20,217 E | 12/1936 | Dunbar |
| 2,229,886 A | 1/1941 | Dunbar |
| 2,494,098 A | 1/1950 | Lockman |
| 2,518,143 A | 8/1950 | Huszar |
| 2,823,118 A | 2/1958 | Merrill |
| 3,025,213 A | 3/1962 | Copeland |
| 3,367,495 A | 2/1968 | Lea et al. |
| 3,823,722 A | 7/1974 | Smith, Jr. |
| 3,991,772 A | 11/1976 | Smith, Jr. |
| 4,032,446 A | 6/1977 | Miller, Jr. |
| 4,050,899 A | 9/1977 | Grube et al. |
| 4,115,695 A | 9/1978 | Kelman |
| 4,178,232 A | 12/1979 | Nollet |
| 4,279,693 A * | 7/1981 | Kuhnlein .............. F23G 7/001 159/16.2 |
| 4,333,611 A | 6/1982 | Zucker et al. |
| 4,540,467 A | 9/1985 | Grube et al. |
| 4,540,495 A | 9/1985 | Holloway |
| 4,622,860 A | 11/1986 | Cametti et al. |
| 4,696,313 A | 9/1987 | Brown et al. |
| 4,757,829 A | 7/1988 | Brown et al. |
| 4,974,780 A | 12/1990 | Nakamura et al. |
| 4,974,781 A | 12/1990 | Placzek |
| 5,050,375 A | 9/1991 | Dickinson |
| 5,100,562 A * | 3/1992 | Proctor ................ B01D 5/0093 210/180 |
| 5,119,994 A | 6/1992 | Placzek |
| 5,134,944 A | 8/1992 | Keller et al. |
| 5,142,830 A | 9/1992 | Carpenter |
| 5,176,793 A | 1/1993 | Kurtz |
| 5,190,226 A | 3/1993 | Holloway |
| 5,217,688 A * | 6/1993 | Von Lersner ....... B02C 19/0075 422/26 |
| 5,253,764 A | 10/1993 | Gement |
| 5,261,225 A | 11/1993 | Dickinson |
| 5,361,994 A | 11/1994 | Holloway |
| 5,383,499 A | 1/1995 | Mattern |
| 5,403,442 A | 4/1995 | Henricson et al. |
| 5,407,817 A | 4/1995 | Lightsey et al. |
| 5,424,033 A | 6/1995 | Roland |
| 5,427,650 A | 6/1995 | Holloway |
| 5,439,556 A | 8/1995 | Sethna et al. |
| 5,445,329 A | 8/1995 | Anderson |
| 5,469,705 A * | 11/1995 | Glenn, Jr. ................ F28B 9/10 60/656 |
| 5,517,004 A | 5/1996 | Blonk |
| 5,540,391 A | 7/1996 | Anderson |
| 5,556,445 A | 9/1996 | Quinn et al. |
| 5,570,845 A | 11/1996 | Lewis et al. |
| 5,602,035 A * | 2/1997 | Sonnen ..................... B09B 3/00 422/184.1 |
| 5,611,673 A | 3/1997 | Agata |
| 5,655,718 A | 8/1997 | Anderson |
| 5,666,878 A | 9/1997 | Taricco |
| 5,705,216 A | 1/1998 | Tyson |
| 5,865,033 A | 2/1999 | Gossler |
| 6,267,309 B1 | 7/2001 | Chieffalo et al. |
| 6,306,248 B1 | 10/2001 | Eley |
| 6,328,234 B1 | 12/2001 | Saucier et al. |
| 6,336,993 B1 | 1/2002 | Stromberg |
| 6,397,492 B1 | 6/2002 | Malley |
| 6,413,364 B1 | 7/2002 | Sandison |
| 6,419,828 B1 | 7/2002 | Russo, Jr. |
| 6,426,136 B1 | 7/2002 | Rouse et al. |
| 6,436,157 B1 | 8/2002 | Winter et al. |
| 6,458,240 B1 | 10/2002 | Bouchette et al. |
| 6,524,436 B2 | 2/2003 | Kettunen et al. |
| 6,555,350 B2 | 4/2003 | Ahring et al. |
| 6,588,690 B1 | 7/2003 | Koenig |
| 6,732,962 B1 | 5/2004 | Butler |
| 6,752,337 B2 | 6/2004 | Koenig |
| 7,497,392 B2 * | 3/2009 | Lee .......................... C10L 5/46 241/21 |
| 7,692,050 B2 * | 4/2010 | Adams ..................... C10G 1/00 585/240 |
| 7,802,694 B2 | 9/2010 | Lee |
| 8,034,132 B2 | 10/2011 | Lee et al. |
| 8,123,864 B2 | 2/2012 | Christensen et al. |
| 8,193,395 B2 | 6/2012 | Fenton et al. |
| 8,236,173 B2 | 8/2012 | Bartek et al. |
| 8,500,910 B2 | 8/2013 | Brady et al. |
| 8,518,132 B2 | 8/2013 | Rettenmaier |
| 8,669,064 B2 | 3/2014 | Steiner et al. |
| 2006/0096163 A1 * | 5/2006 | Dickinson ................ C10G 1/02 44/552 |
| 2006/0260186 A1 | 11/2006 | Iversen et al. |
| 2007/0017192 A1 * | 1/2007 | Bednarek ................. B01D 1/28 55/405 |
| 2007/0190643 A1 | 8/2007 | Noll |
| 2008/0014112 A1 * | 1/2008 | Lee .......................... C10L 5/46 422/26 |
| 2008/0051620 A1 * | 2/2008 | Deyerling ............... C12M 29/06 588/251 |
| 2008/0096787 A1 * | 4/2008 | Cauley .................... C10B 53/07 510/407 |
| 2009/0062581 A1 | 3/2009 | Appel et al. |
| 2009/0081091 A1 | 3/2009 | Lee |
| 2009/0215000 A1 * | 8/2009 | Boots ........................ B09B 3/00 432/118 |
| 2011/0121112 A1 | 5/2011 | Alford |
| 2012/0318017 A1 * | 12/2012 | Cheng ................. B01D 5/0006 62/601 |
| 2013/0305599 A1 | 11/2013 | Rettenmaier |
| 2014/0060049 A1 * | 3/2014 | Conry ..................... F01K 11/02 60/650 |
| 2014/0363856 A1 | 12/2014 | Sisson et al. |

FOREIGN PATENT DOCUMENTS

| | | |
|---|---|---|
| EP | 0908190 A2 | 4/1999 |
| EP | 1978086 A1 | 10/2008 |
| GB | 450209 | 7/1936 |
| GB | 2370242 A | 6/2002 |
| JP | 2001039787 A | 2/2001 |
| JP | 2004108727 A | 4/2004 |
| JP | 2004130235 A | 4/2004 |
| WO | WO9400162 A1 | 1/1994 |
| WO | WO9513148 A1 | 5/1995 |
| WO | WO03035970 A1 | 5/2003 |
| WO | WO-2013092881 A2 * | 6/2013 ............. C12P 19/02 |

* cited by examiner

METHODS AND APPARATUS UTILIZING VACUUM FOR BREAKING ORGANIC CELL WALLS

BACKGROUND

Methods and apparatus utilizing vacuum below atmospheric pressure for treatment of organic material to break cell walls to maximize output of conversion technologies by increasing the available processable free sugars and surface area are shown and described.

Various techniques have arisen for processing of waste organic materials to minimize use of landfills and environmental impact, with such waste being generated by commercial businesses, farms, poultry or livestock facilities, as well as municipalities. Further, in an effort to produce viable and market competitive energy products from that waste and reduce dependence upon fossil fuels, various conversion techniques have arisen to convert organic material into process engineered feedstocks (PEF). The field has recognized that the transformation resulting from placing organic material under increased pressure by the application of heat enhances downstream processing of such organic material. U.S. Pat. No. 7,497,392 represents a technique which has shown favorable results, but which suffers from several drawbacks, which have affected its acceptance and marketability. Specifically, the major drawbacks are inherent due to pressurizing. First, in order to generate the increased pressure required, large amounts of heat are required to generate the necessary pressure, which is counterproductive to maximizing the net energy production of PEF. Further, to produce the necessary pressure, large amounts of moisture must be added in the form of steam or water, which increases the amount of energy required to heat the added moisture and the organic material to break down the organic materials. Additionally, the processed material is at an elevated temperature which may be required to be cooled for handling or further processing. Furthermore, as increased pressure is involved, the components, especially the pressure vessel, must be more robust to handle the pressures involved, which increases cost of material and complicates assembly.

Additionally, vacuum pumps are utilized to reduce pressure such as in vessels in prior conversion techniques and must be protected against moisture reaching the vacuum pump to increase its operational life and efficiencies. Although various condensers have been developed, the field has recognized that further development would be desired.

Furthermore, water is supplied at variable and different temperatures. The amount of input energy required to operate is directly related to the cost effectiveness. Thus, there is a need to recapture heat from the vapor stream passing through a moisture collector before a vacuum pump to heat the water to be supplied to the process.

Thus, a need has arisen to pre-treat organic material before conversion technologies that avoids the drawbacks encountered by the conventional organic material pressure treatment and that maximizes the output of conversion technologies by increasing the processable free sugars and convertible organics surface area. Further, a need has arisen to collect moisture from a process flow stream and before reaching a vacuum pump, especially when creating a vacuum below atmospheric pressure, as well as to recapture heat from the vapor stream leaving the process vessel to heat the fluid utilized to moisturize the organic material.

SUMMARY

In order to solve this and other needs in the field of treatment of organic material, methods and apparatus utilize vacuum below atmospheric pressure for breaking cell walls in organic material to increase available processable free sugars and convertible surface area to maximize output of conversion technologies. Specifically, organic waste is treated by methods and apparatus which subject moisturized organic material to a deep vacuum below atmospheric pressure for a processing period of time, with the vacuum applied being sufficiently below atmospheric pressure during that period of time to bring the latent moisture content entrained in the organic material to a vaporization point to create an internal pressure in the moisturized organic material to rupture cell walls of the moisturized organic material. The moisturized organic material is homogenized while being subjected to the vacuum, such as by rotating the vessel containing the moisturized organic material.

If the ambient temperature of the moisturized organic material is below the vaporization point, heat can be added to the moisturized organic material to reduce the vacuum subjected to the moisturized organic material.

Moisture collected by a moisture collector in a conduit between the vessel containing the moisturized organic material and the vacuum pump can be conveyed to a source of moisture for moisturizing the organic material, such as non-potable water, to 85 to 100% of the dry weight of the organic material. The moisture collector includes an inlet valve in communication with a collection tank through which the flow stream passes and which includes a heat exchanger and in communication with a condensation accumulator. The condensation accumulator includes a normally closed outlet valve. The inlet valve is normally open and closes when moisture accumulates in the condensation accumulator and the outlet valve opens.

Fluid from a feed tank is chilled and simultaneously flows to a vacuum pump and a heat exchanger inside of a collection tank of a moisture collector. The chilled fluid inside the vacuum pump acts as the seal fluid inside the vacuum pump and is blended with the vapor stream leaving the vacuum pump to return to the feed tank. The chilled fluid flowing through the heat exchanger receives heat from the vapor stream flowing through the collection tank. Condensed moisture is drained from the collection tank.

The treated organic material is delivered for further processing, including, but not limited to, the destruction of pathogens contained therein such as by pasteurization and sterilization.

The detailed description of illustrative embodiments and some of the advantages gained thereby will become clearer in connection with and in light of the drawings.

DESCRIPTION OF THE DRAWINGS

The illustrative embodiments may best be described by reference to the accompanying drawings where.

All figures are drawn for ease of explanation of the basic teachings only; the extensions of the figures with respect to number, position, relationship, and dimensions of the parts to form the illustrative embodiments will be explained or will be within the skill of the art after the following description has been read and understood. Further, the exact dimensions and dimensional proportions to conform to specific force, weight, strength, and similar requirements will likewise be within the skill of the art after the following description has been read and understood.

Where used in the various figures of the drawings, the same numerals designate the same or similar parts. Furthermore, when the terms "top", "bottom", "first", "second", "forward", "rearward", "reverse", "front", "back", "height", "width", "length", "end", "side", "horizontal", "vertical", and similar terms are used herein, it should be understood that these terms have reference only to the structure shown in the drawings as it would appear to a person viewing the drawings and are utilized only to facilitate describing the illustrative embodiments.

DESCRIPTION OF THE ILLUSTRATIVE EMBODIMENTS

An illustrative embodiment of an apparatus for treatment of organic material by methods to maximize output of conversion technologies by increasing the available free sugars and surface area of the organic materials is shown in the drawings and generally designated 10. The organic materials to be treated include, but are not limited to, manure, carcasses, and agricultural products and residues. Further, organic material to be treated could include municipal solid waste. In this regard, the organic material could be included with other inorganic materials such as metals, glass and the like. It should be appreciated that throughput will be a function of the amount of organic material being processed, and that sorting and segregating inorganic material can be accomplished before and/or after treatment by apparatus 10 according to various parameters. In this regard, organic material from which inorganic material has been removed and/or from a specific source to have relatively constant characteristics provide enhanced operational efficiency.

Apparatus 10 includes a processing vessel 12 which for purposes of reduction to practice is similar to that shown and disclosed in U.S. Pat. No. 7,802,694, which is hereby incorporated herein by reference. Specifically, vessel 12 defines a first end 14 and an opposite, second end 16. Vessel 12 has an exterior wall 18 surrounding and defining an interior volume 20. At first end 14, vessel 12 includes a movable door 22 to provide selective access to interior volume 20 and allow for loading of waste material into volume 20. Door 22 is selectively closeable to prevent access to interior volume 20. Door 22 is described in U.S. Pat. No. 7,802,694, which is incorporated herein by reference. However, door 22 can be of different forms and/or types.

In general, in one embodiment, vessel 12 is of a size such that the distance between first end 14 and second end 16 is about 27 feet (9 meters), and the diameter of vessel 12 is about 8 feet (2.6 meters). The size of the open interior volume 20 is about 1200 cubic feet (34,000 liters). However, it should be appreciated that size is based upon various parameters and may be dependent upon the particular form of organic material to be treated and the desired throughput. Furthermore, vessel 12 can be of a variety of forms and types for batch and continuous processing which subject the organic materials contained therein to a vacuum below atmospheric pressure for sufficient time to complete treatment thereof.

Figure 1:
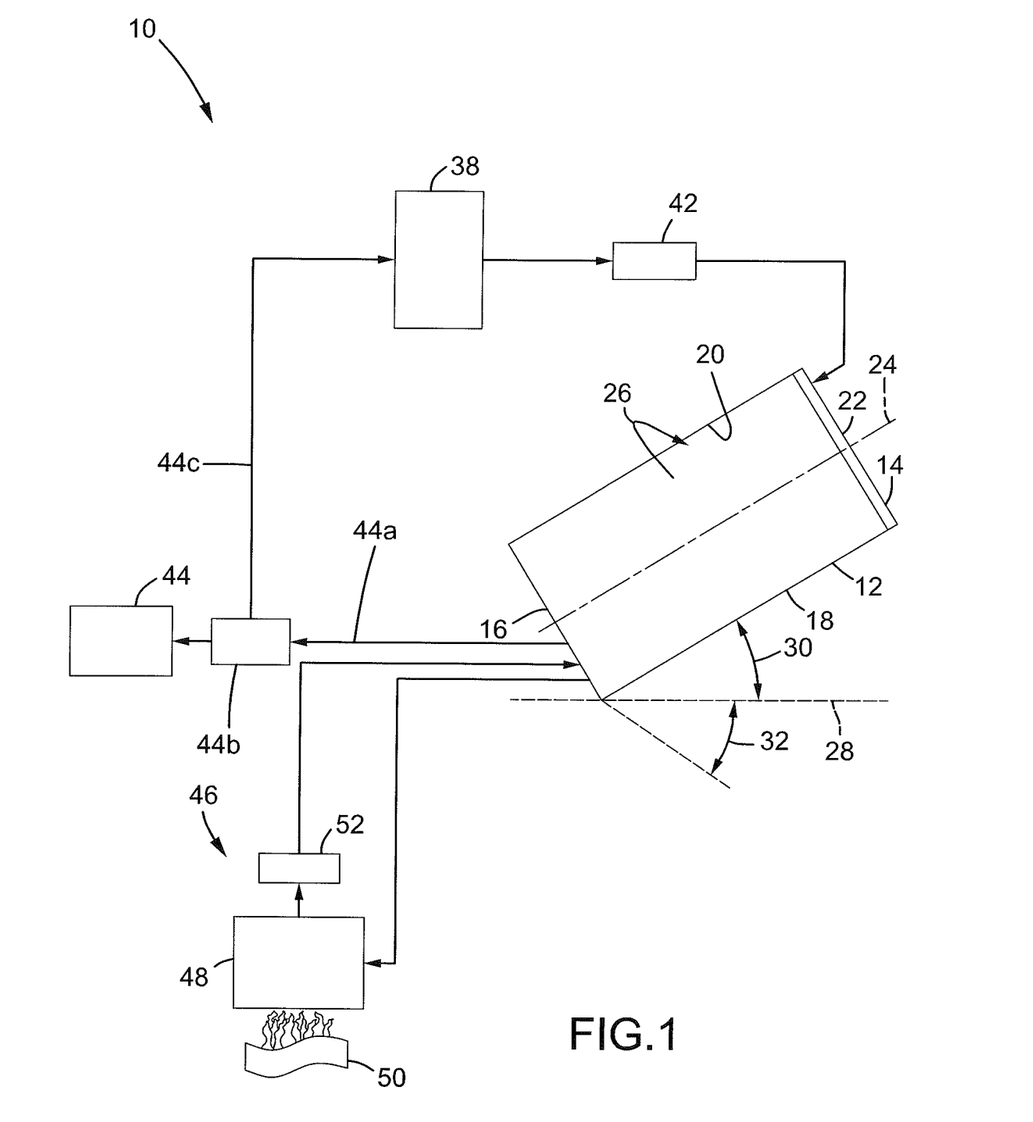
FIG. 1 shows a diagrammatic view of an illustrative embodiment of an apparatus utilizing vacuum below atmospheric pressure for treatment of organic material.

Vessel 12 is rotatable about a central longitudinal axis 24. In FIG. 1, arrow 26 indicates the rotatable motion of vessel 12 about axis 24. Vessel 12 is rotatable at a speed of about −16 to about 16 RPM, to cause the interior contents of vessel 12 (usually organic material) to rotate to agitate and homogenize the organic material. It should be appreciated that agitation and/or homogenization can be performed in other manners and/or with other types and forms of construction.

Vessel 12 is tiltable or moveable between material treatment conditions such as at least a load position, a treatment position, and a discharge position. In FIG. 1, vessel 12 is shown in the load position. In this position, material is loaded into interior volume 20 through an opening in the vessel created by moving door 22. Vessel 12 is moved from the horizontal, represented here by reference numeral 28 at an angle 30. Angle 30 is an angle sufficient to allow for material to be loaded in interior volume 20 to allow it to fill interior volume 20. Angle 30 also depends upon the height of the mechanism, such as a conveyor, loading the material into vessel 12. One useable angle for angle 30 is at least 30°, not greater than 115°, for example about 35°-50°, and in one instance, about 40°. As should be appreciated from FIG. 1, when vessel 12 is in the loading position, first end 14 including door 22 is higher than second end 16, which is also a closed end.

In the treatment position, first end 14 and second end 16 are close to horizontally even, such that longitudinal axis 24 of vessel 12 is about parallel to horizontal 28.

The discharge position includes vessel 12 lowered at an angle 32. In the discharge position, first end 14 is horizontally lower than second end 16. The discharge position allows the contents of interior volume 20 to be removed from vessel 12 through the opening created by door 22. Angle 32 can be −5 to −60°, for example −10° to −40°, and preferably −12° to −20°.

However, it should be appreciated that processing vessel 12 can take other forms and types which allow loading, treatment, and discharge of organic material as well as which allow for a vacuum to be applied and maintained to the organic material for the treating process and time. In this regard, processing vessels 12 could be stationary and include moveable or stationary mixing devices. Furthermore, processing vessels 12 could be of the batch or continuous processing type.

Apparatus 10 further includes a source of moisture 38 and a delivery device 42 for delivering the moisture to vessel 12. Source of moisture 38 in preferred aspects is a tank of non-potable water, but potable water could be utilized as well. Delivery device 42 could be a pump for conveying moisture into vessel 12 to provide a saturation of moisture to be absorbed and entrained in the organic material.

A vacuum pump 44 is provided in vacuum communication by a conduit 44a with interior volume 20 of vessel 12. Vacuum pump 44 depicted will selectively reduce pressure below atmospheric pressure within interior volume 20 of vessel 12. As it is undesired to have steam pass through vacuum pump 44, a moisture collector 44b is provided in conduit 44a intermediate and spaced from the moisturized organic material in vessel 12 and pump 44 for collecting moisture from the flow stream. Moisture collected by collector 44b can be suitably conveyed to source of moisture 38 such as through conduit 44c.

Figure 3:
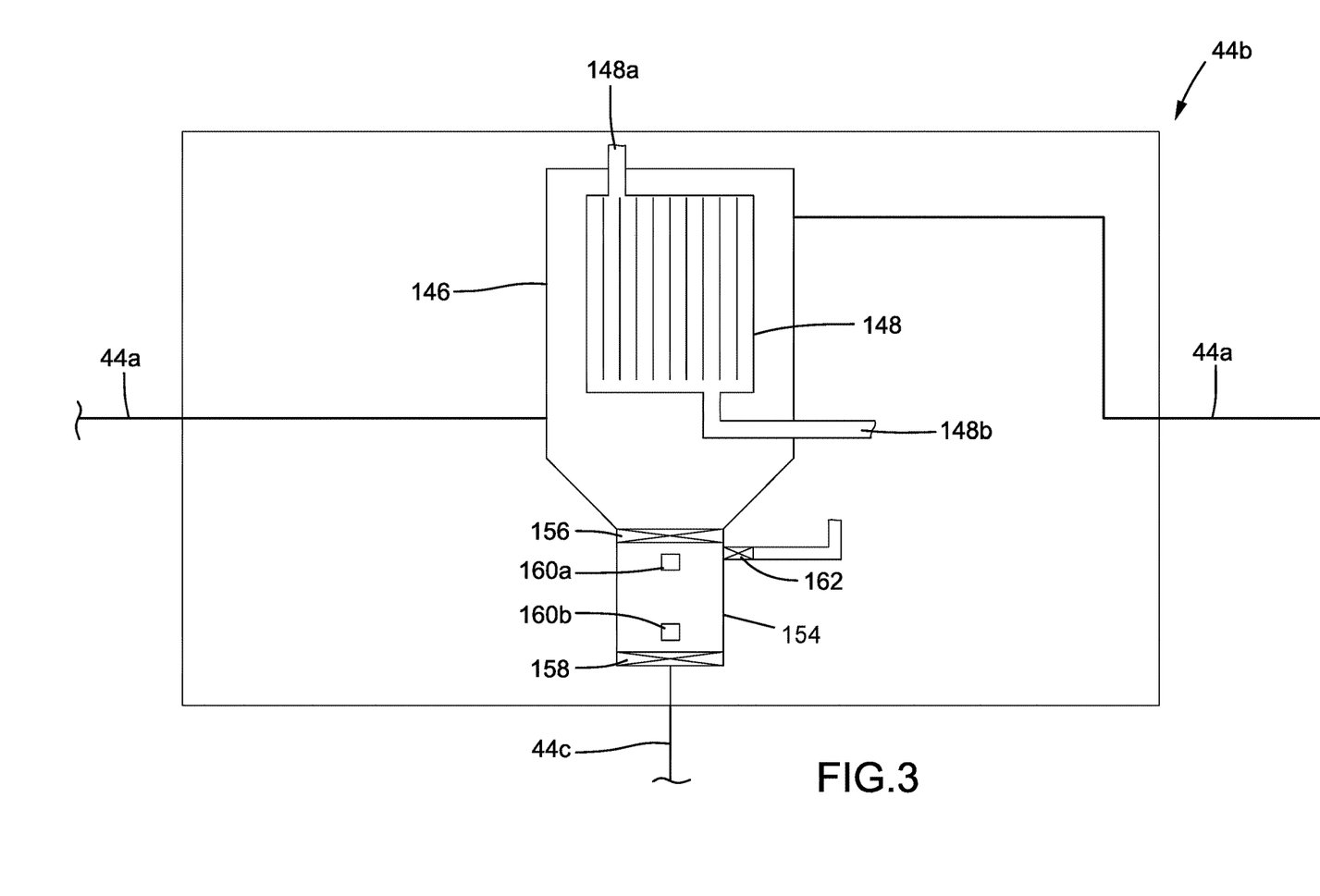
FIG. 3 shows a diagrammatic view of a moisture collector.

In an exemplary form shown in FIG. 3, moisture collector 44b includes a filter and a collection tank 146 in conduit 44a intermediate vacuum pump 44 and vessel 12, with the filter being intermediate vessel 12 and collection tank 146. The filter can be a metal mesh or can be of any form for removing solids flowing out of vessel 12 in the flow stream. A heat exchanger 148 is provided inside of collection tank 146 for cooling the flow stream and condensing the moisture located in the flow stream as it is being drawn through collection tank 146 and past heat exchanger 148. In an exemplary form, heat exchanger 148 is of the fluid type and includes an inlet 148a receiving cold fluid such as water and an outlet 148b allowing the fluid heated by the flow stream to exit. In the case of water, inlet 148a could be in fluid communication with a well or other source of water below atmospheric temperature, and outlet 148b could be in fluid communication with source of moisture 38. In the case of fluids, heat exchanger 148 could be either of the plate or tube type, but heat exchanger 148 can be of any form suitable for condensing moisture located in the flow stream. Moisture collector 44b further includes a condensation accumulator 154 including an inlet valve 156 in fluid communication with a lower portion of collection tank 146 to provide fluid communication between collection tank 146 and condensation accumulator 154 when desired. An outlet valve 158 is in fluid communication with condensation accumulator 154 and conduit 44c to provide fluid communication between condensation accumulator 154 and source of moisture 38 to drain the condensed moisture from inside collection tank 146 when desired by gravity or pumping. Condensation accumulator 154 further includes a high and low level switch sensor 160a and 160b as well as a relief valve 162 in fluid communication with condensation accumulator 154.

Water can be supplied at different temperatures depending on where in the world apparatus 10 is located. As an example, ground water and municipal water can vary in temperature from about 40° F. (4.5° C.) to about 60° F. (15.5° C.). If the water is supplied from a feed water tank 170 holding the water, the temperatures can vary even more. Therefore to create constant feed water temperature, an exemplary form of apparatus 10 shown in FIG. 4 utilizes a chiller 172 in fluid communication with feed water tank 170 to create a constant water supply of 40° F. (4.5° C.) water. Water is pumped and flows from feed water tank 170 through a pump 174 that supplies chiller 172. Chiller 172 can be of any form, such as conventional electrically powered, which cools the water to around 40° F. (4.5° C.). Chiller 172 is in fluid communication with both vacuum pump 44 and heat exchanger 148. The water is then split and flows into a supply line 176a and inlet 148a that feed both vacuum pump 44 and moisture collector 44b, respectively, simultaneously. Water flowing to vacuum pump 44 through supply line 176a becomes the seal water to create a vacuum, is blended with the warm vapor coming from moisture collector 44b inside of vacuum pump 44, and is returned to feed water tank 170 through a return line 176b providing fluid communication between vacuum pump 44 and feed water tank 170. This return water is then recycled back to chiller 172, and this portion of the cycle remains as a closed loop. The chilled water fed through inlet 148a to moisture collector 44b is heated as it passes through heat exchanger 148 and then flows out of outlet 148b and is fed into source of moisture 38 through outlet 148b. The energy leaving vessel 12 in the form of heated steam vapor is transferred into the chilled feed water. The vapor chilled in moisture collector 44b gathers in condensation accumulator 154 and is drained through conduit 44c to source of moisture 38. The heat recaptured in moisture collector 44b will enable the process to increase the efficiency by preheating the process water. Thus, the process will not need as much additional heat to reach the process temperatures required. Water will be warmed as little as 20° F. (10° C.) and as much as 120° F. (67° C.). By doing this, the process re-captures as much as little as 10% and as much as 25% of the input energy from vessel 12. Thus, utilizing chiller 172 enhances operation of moisture collector 44b to improve energy transfer and to protect vacuum pump 44 and stabilize the temperatures of the water feeding apparatus 10.

Figure 4:
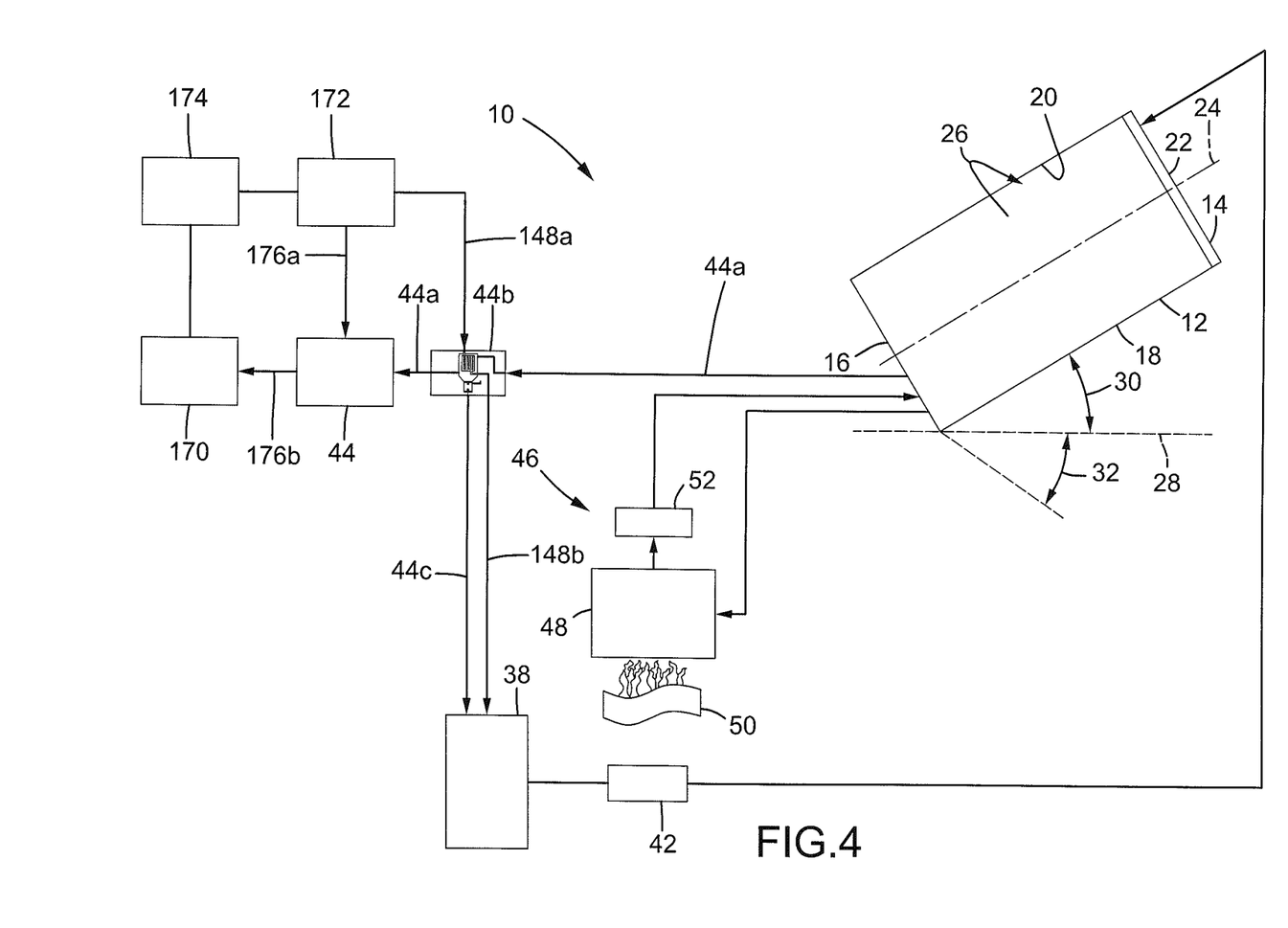
FIG. 4 shows a diagrammatic view of an illustrative embodiment of an apparatus utilizing vacuum below atmospheric pressure for treatment of organic material.

A heater 46 is provided to increase the temperature of interior volume 20 of vessel 12. In the embodiment shown in FIG. 1 and/or 4, heater 46 includes a working fluid, for example, a tank of oil 48, which is heated by, in the embodiment shown, a burner 50. A pump 52 conveys heated oil 48 from its tank to vessel 12. Vessel 12 includes internal conduits arranged helically or in a coil to circulate heated oil 48 through interior 20 of vessel 12. In this way, the heated oil does not itself mix up with the contents of vessel 12. Rather, heated oil 48 is circulated through the conduits to allow for the heat carried by oil 48 to transfer from oil 48 to the contents of interior volume 20 of vessel 12. Oil 48 is circulated within vessel 12 and returned to the tank to allow it to be reused, so that hot oil 48 is always being conveyed and circulated through vessel 12 during the appropriate heating stage. However, other manners of adding heat can be utilized instead of or in addition to that shown. As an example, the source of moisture 38 could be heated before its introduction to vessel 12.

Figure 2:
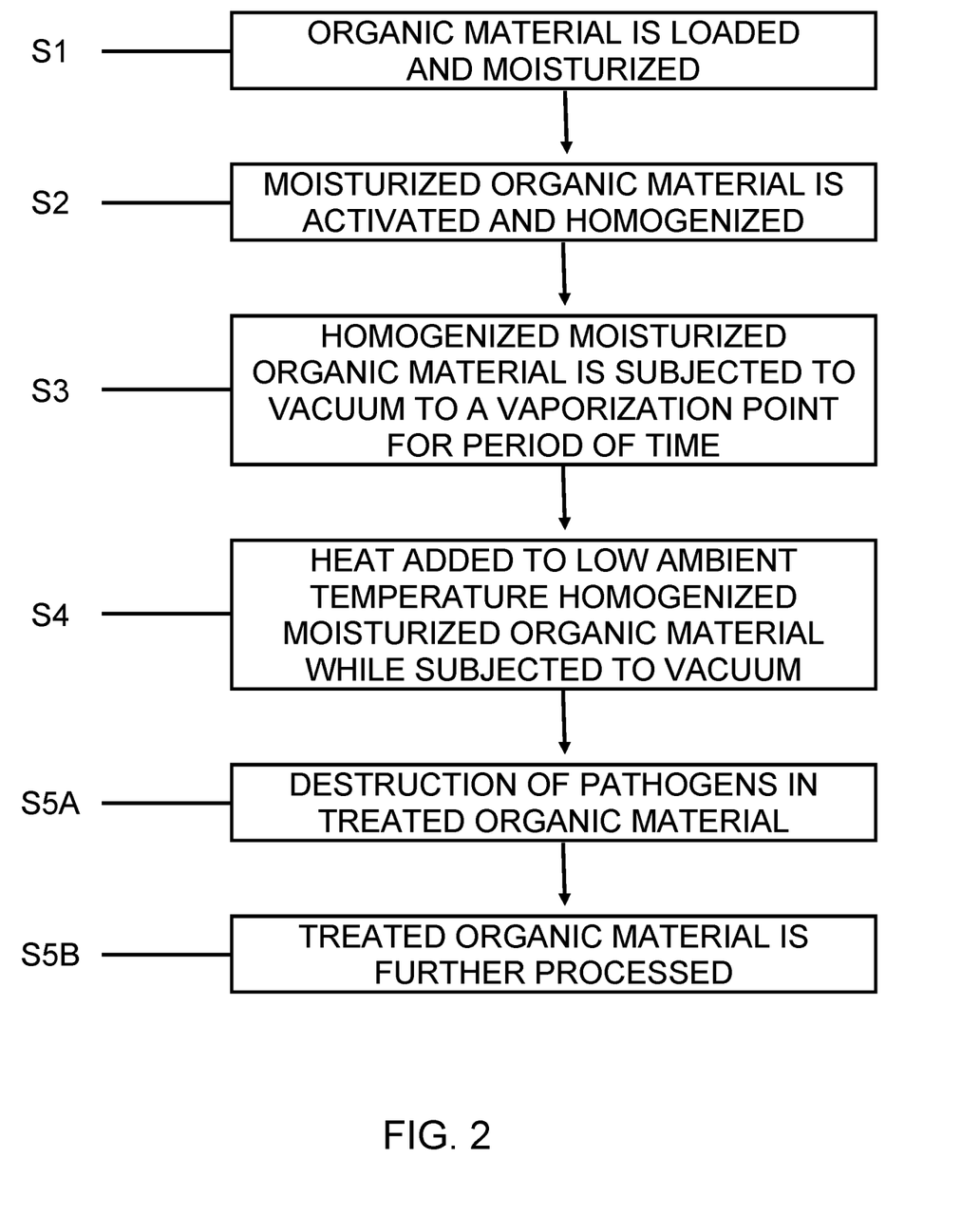
FIG. 2 shows a block diagram of an illustrative method utilizing vacuum below atmospheric pressure for treatment of organic material.

A method or process for treating organic material is shown in FIG. 2. In step S1, organic material is loaded into processing vessel 12 and moisture such as non-potable water is introduced from source of moisture 38 into processing vehicle 12 at a ratio to bring the minimum moisture content to 75% to 125% of the dry weight for some feedstocks and generally 75% to 100% of the dry weight of the organic material. In step S2, the organic material and moisture is homogenized such as by rotating processing vessel 12 with the moisturized organic material therein. After processing vessel 12 is closed and sealed, such as by closing door 22, and in step S3, vacuum pump 44 is actuated to reduce the pressure inside of interior volume 20 below atmospheric pressure or in other words subject the moisturized organic material to a deep vacuum below atmospheric pressure sufficient to reduce the boiling point of the latent moisture content entrained in the moisturized organic material to a processing boiling or vaporization point of approximately 104° F. (40° C.) or less, and, particularly 86 to 64° F. (30 to 17.8° C.) for minimizing the total amount of energy required to draw the vacuum or heat the moisturized organic material for a period of time and while moisturized organic material is being homogenized. Specifically, in apparatus 10 of FIGS. 1 and/or 4, interior volume 20 of vessel 12 is subjected to a vacuum of approximately 27.75 inches (704.85 mm) of mercury or greater and in particular to 28.67 to 29.32 inches (728.22 to 744.73 mm) of mercury below atmospheric pressure. In this regard, if the ambient temperature of the organic material and moisture is at the processing boiling or vaporization point to cause rupturing cell walls, heat does not need to be added. However, the ambient air temperature in which vessel 12 is located and/or the ambient temperature of the organic material and moisture, such as a result of being stored outdoors in winter climates, could be relatively low in comparison to the processing boiling or vaporization point. If the ambient temperature of the organic material and moisture entering processing vessel is below the prescribed processing boiling or vaporization point, heat is added to the organic material and moisture such as by circulating heated oil 48 within vessel 12. Typically heat is not added until after pressure is reduced inside of vessel 12 below atmospheric pressure and the presence of moisture is detected at moisture collector 44b. When the processing boiling or vaporization point is reached inside of vessel 12, the moisture latent within the organic material will form a gas (steam). Steam expands rapidly when formed from water, creating an internal pressure in the moisture laden organic material. This rapid expansion and internal pressure ruptures the cell walls of the organic material, breaking it down rapidly. With the proper agitation and homogenizing, treatment processing will be accomplished in as fast as 5 to 25 minutes, in approximately 10 to 40 minutes, and particularly in 10 to 30 minutes. It should be appreciated that the moisturized organic material is subjected to a vacuum below atmospheric pressure for at least 95% of the process time while the moisture latent within the organic material is being formed into steam.

Any steam or moisture removed from vessel 12 by vacuum pump 44 can be re-condensed out of conduit 44a before vacuum pump 44 and returned to source of moisture 38 by moisture collector 44b. In operation, inlet valve 156 is open, and valves 158 and 162 are closed. The flow stream in conduit 44a first has any solids removed when passing through the filter. When passing into collection tank 146, moisture will condense on heat exchanger 148 and will pass through inlet valve 156 into condensation accumulator 154. When the level of moisture collected reaches high level switch sensor 160a, inlet valve 156 is closed, and valves 158 and 162 are opened, allowing moisture collected in condensation accumulator 154 to drain into conduit 44c and into source of moisture 38. When the level of the moisture in the condensation accumulator 154 reaches low level switch sensor 160b, valves 158 and 162 are again closed, and inlet valve 156 opened to repeat the cycle. It should be appreciated that by closing inlet valve 156, interference with or blocking the drawing of vacuum pump 44 does not occur. Further, the condensation accumulator 154 acts as a sealed catch basin/trap of a sufficient volume to pool generally continuously during operation of vacuum pump 44.

After treatment processing has been completed, the treated organic material is delivered in Step S4 such as by being discharged from vessel 12 such as by being unloaded or evacuated. The discharged material is then further processed in Step S5B such as by being sorted, being conveyed to anaerobic digesters or other types of conversion technologies in the form of a PEF or the like. Further processing can include the destruction of pathogens in step S5A which is a function of time and temperature such as, but not limited to, by pasteurization and sterilization, during or after treatment processing and while in vessel 12 and/or after its discharge from vessel 12. In this regard, the treatment processing concentrates the treated organic material while pasteurizing at lower temperatures.

Now that the basic construction and method has been set forth, some of the features and advantages can be set forth and highlighted. Using a reduction in pressure below atmospheric pressure to process organic material is a major departure from conventional processing utilizing heat to increase pressure. Specifically, the energy requirements for operating vacuum pump 44 is significantly less than for heating the organic material, and recapturing heat from the process stream preheats and stabilizes the feed water temperature and enhances operation of the moisture collector 44b to protect the vacuum pump 44. Further, although heat may be necessary depending upon the ambient temperature of the organic material and moisture introduced into vessel 12, the amount of heat needed can be related to the amount of vacuum reduction and significantly reduces the energy required in comparison to the conventional increased pressure systems. Additionally, as indicated previously, the vacuum reduction method concentrates the value producing aspects of organic materials whether in a form of a liquid or a solid. Furthermore, the construction and materials for forming vessel 12 and apparatus 10 can be of a lesser grade than conventional pressure vessels and systems. Thus, the cost and assembly requirements are reduced. Furthermore, no chemicals or additives (aside from moisture such as in the form of any source of non-potable water) are needed to break down organics, and the vacuum reduction method does not affect inorganic materials but results in rapid breakdown of organic materials to enhance yield of down stream processes.

Although apparatus 10 including moisture collector 44b is believed to produce synergistic results, apparatus 10 can be utilized with other types and methods of moisture collection. Similarly, moisture collector 44b can be utilized with other types and forms of organic material treatment apparatus and/or with other types of vacuum apparatus requiring moisture collection to protect the vacuum pump. Likewise, the heat recapture device can be utilized with other types and forms of moisture collectors and/or with other types and forms of organic material treatment apparatus and/or with other types of vacuum apparatus requiring moisture collection to protect the vacuum pump.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

The invention claimed is:

1. Method of treating organic material comprising:
    moisturizing organic material to a latent moisture content entrained in the organic material, wherein moisturizing the organic material comprises adding water to the organic material;
    subjecting the moisturized organic material to a vacuum below atmospheric pressure for a period of time of approximately 5 to 40 minutes with the vacuum being sufficiently below atmospheric pressure to bring the latent moisture content to a vaporization point;
    homogenizing the moisturized organic material while the moisturized organic material is being subjected to the vacuum below atmospheric pressure, with the period of time being sufficient to create an internal pressure in the moisturized organic content to rupture cell walls of the moisturized organic material to provide treated organic material; and
    delivering the treated organic material to further processing.

2. The method as defined in claim 1 wherein moisturizing the organic material comprises adding the water to bring the latent moisture content from a 75% to 125% of a dry weight of the organic material.

3. The method as defined in claim 2 wherein subjecting the moisturized organic material to the vacuum comprises:
    operating a vacuum pump in vacuum communication by a conduit with the moisturized organic material;
    flowing a vapor stream through the conduit past a heat exchanger inside a collection tank;
    while flowing the vapor stream, flowing the water into an inlet of the heat exchanger, through the heat exchanger 
and out an outlet of the heat exchanger for use in moisturizing the organic material, with a temperature of the water being higher at the outlet of the heat exchanger than at the inlet of the heat exchanger to condense moisture inside the collection tank;

passing the moisture inside the collection tank through an inlet valve of a condensation accumulator; and closing the inlet valve and opening an outlet valve of the condensation accumulator when the moisture in the condensation accumulator reaches a first level and closing the outlet valve and opening the inlet valve when the moisture in the condensation accumulator reaches a second level, with the second level being below the first level, wherein moisturizing the organic material includes moisturizing the organic material with the moisture flowing from the outlet valve.

4. Method of treating organic material comprising:

flowing a vapor stream through a conduit past a heat exchanger inside a collection tank and while flowing the vapor stream, flowing fluid into an inlet of the heat exchanger, through the heat exchanger and out an outlet of the heat exchanger, with temperature of the fluid being higher at the outlet of the heat exchanger than at the inlet of the heat exchanger to condense moisture inside the collection tank;

passing the condensed moisture inside the collection tank through an inlet valve of a condensation accumulator;

closing the inlet valve and opening an outlet valve of the condensation accumulator when the condensed moisture in the condensation accumulator reaches a first level and closing the outlet valve and opening the inlet valve when the condensed moisture in the condensation accumulator reaches a second level, with the second level being below the first level, wherein flowing the fluid comprises: flowing the fluid in a form of water into the inlet of the heat exchanger and flowing the condensed moisture from the outlet valve for moisturizing the organic material;

operating a vacuum pump in vacuum communication by the conduit with the moisturized organic material, with the organic material moisturized to a latent moisture content entrained in the organic material;

subjecting the moisturized organic material to a vacuum below atmospheric pressure for a period of time of approximately 5 to 40 minutes with the vacuum being sufficiently below atmospheric pressure to bring the latent moisture content to a vaporization point;

homogenizing the moisturized organic material while the moisturized organic material is being subjected to the vacuum below atmospheric pressure, with the period of time being sufficient to create an internal pressure in the moisturized organic material to rupture cell walls of the moisturized organic material to provide treated organic material; and delivering the treated organic material to further processing.

5. The method as defined in claim 4, wherein opening the outlet valve includes opening a relief valve in fluid communication with the condensation accumulator, and wherein closing the inlet valve comprises providing high and low level switch sensors sensing the first and second levels, with the high level switch sensor causing the inlet valve to close and the low level switch causing the outlet valve to close.

6. The method as defined in claim 4 further comprising:
supplying the water to a feed tank;
flowing the water from the feed tank to a chiller;
cooling the water in the chiller;
flowing the cooled water from the chiller to the vacuum pump, with the cooled water inside the vacuum pump acting as a seal fluid, with the cooled water blended with the vapor stream inside the vacuum pump;
flowing the blended cooled water and the vapor stream from the vacuum pump back to the feed tank; and
flowing the cooled water from the chiller into the heat exchanger, with the flowing fluid flowing out of the exchanger and out of the outlet valve moisturizing the organic material.

7. The method as defined in claim 4 further comprising:
heating the moisturized organic material while the moisturized organic material is being subjected to the vacuum below atmospheric pressure to reduce the vaporization point to between 30 to 17.8° C.

8. The method as defined in claim 7 wherein homogenizing the moisturized organic material comprises containing the moisturized organic material in a sealed vessel and rotating the sealed vessel with the moisturized organic material contained therein.

9. The method as defined in claim 8 wherein heating the moisturized organic material comprises heating a working fluid and circulating the heated working fluid in internal conduits in the sealed vessel.

10. The method as defined in claim 4 further comprising:
adding heat to the moisturized organic material when an ambient temperature of the moisturized organic material is below the vaporization point.

11. The method as defined in claim 4 wherein flowing the fluid in the form of water comprises flowing the fluid in the form of water which is non-potable water to the organic material.

12. The method as defined in claim 4 further comprising:
adding heat for a period of time to the treated organic material sufficient to destroy pathogens in the treated organic material.

13. Apparatus for treating organic material including: a collector comprising a collection tank, a heat exchanger inside of the collection tank, with the collection tank in fluid communication with a conduit, a condensation accumulator, an inlet valve in communication with the collection tank and the condensation accumulator, and an outlet valve in communication with the condensation accumulator, with the inlet valve being normally open and closed when the outlet valve is open, with the outlet valve being normally closed, wherein the heat exchanger is a fluid heat exchanger including an exchanger inlet and an exchanger outlet, with fluid flowing through the fluid heat exchanger having a higher temperature at the exchanger outlet than at the exchanger inlet; a vessel receiving the organic material; a source of moisture delivered into the vessel with the organic material; and a vacuum pump in vacuum communication by the conduit with an interior volume of the vessel and subjecting the organic material and the moisture in the vessel to vacuum lower than atmospheric pressure to bring a latent moisture content of the organic material and the moisture in the vessel to a vaporization point for a period of time, with the organic material with the latent moisture content being homogenized in the vessel during the period of time, with the conduit intermediate the interior volume and the vacuum pump, with the outlet valve in communication with the source of moisture, and with the exchanger outlet in fluid communication with the source of moisture; and combination: a feed tank holding fluid; and a chiller in fluid communication with the feed tank, with the chiller in fluid communication with the vacuum pump, with the fluid being chilled in the chiller and acting as a seal fluid inside the vacuum pump, with the vacuum pump in fluid communication with the feed tank to return the chilled fluid and vapor from the collection tank to the feed tank, with the chiller in fluid communication with the heat exchanger, with the heat exchanger and the outlet valve in fluid communication with the source of moisture.

14. The apparatus as defined in claim 13 wherein the moisture collector further comprises a relief valve in fluid communication with the condensation accumulator, with the relief valve being normally closed and opened when the outlet valve is opened, with the condensation accumulator including high and low level switch sensors, with the high switch sensor causing the inlet valve to close and the low level switch sensor causing the outlet valve to close.

15. The apparatus as defined in claim 13 further comprising, in combination: a heater heating the vessel and the organic material and the moisture contained therein while being subjected to the vacuum lower than atmospheric pressure by the vacuum pump.

16. The apparatus as defined in claim 15 wherein the heater comprises a source for working fluid to be circulated with the vessel to transfer heat from the working fluid to the organic material and the moisture.

17. The apparatus as defined in claim 13 further comprising means moving the organic material and the moisture relative to the vessel for homogenizing the organic material and the moisture in the vessel.

18. The apparatus as defined in claim 13 wherein the vessel includes a movable door providing selective and sealable access to an interior volume of the vessel receiving the organic material and the moisture and includes a central longitudinal axis, with the vessel rotatable about the central longitudinal axis.

* * * * *